(12) United States Patent
Miller

(10) Patent No.: US 11,635,073 B2
(45) Date of Patent: Apr. 25, 2023

(54) LINEAR PERISTALTIC PUMP

(71) Applicant: FLEX Ltd., Singapore (SG)

(72) Inventor: John Patrick Miller, Edmond, OK (US)

(*) Notice: Subject to any disclaimer, the term of this patent is extended or adjusted under 35 U.S.C. 154(b) by 561 days.

(21) Appl. No.: 15/844,864

(22) Filed: Dec. 18, 2017

(65) Prior Publication Data

US 2019/0186484 A1 Jun. 20, 2019

(51) Int. Cl.
*F04B 43/12* (2006.01)
*F04B 43/08* (2006.01)

(52) U.S. Cl.
CPC ........ *F04B 43/1261* (2013.01); *F04B 43/082* (2013.01); *F04B 43/1223* (2013.01); *F04B 43/1276* (2013.01)

(58) Field of Classification Search
CPC .... F04B 43/01; F04B 43/0081; F04B 49/065; F04B 43/0072; F04B 43/1276; F04B 43/1261; F04B 43/082; F04B 43/1223
See application file for complete search history.

(56) References Cited

U.S. PATENT DOCUMENTS

| | | | | |
|---|---|---|---|---|
| 4,482,347 A * | 11/1984 | Borsanyi | ........... | A61M 5/14228 604/153 |
| 4,493,706 A * | 1/1985 | Borsanyi | ........... | A61M 5/142 128/DIG. 12 |
| 4,809,562 A * | 3/1989 | Bendoraitas | ........... | F01L 1/047 74/567 |
| 4,847,963 A * | 7/1989 | Bendoraitas | ........... | F01L 1/047 29/888.1 |
| 4,873,915 A * | 10/1989 | Newman | ........... | A47J 31/3628 99/289 R |
| 5,078,683 A * | 1/1992 | Sancoff | ........... | A61M 5/14228 604/67 |
| 5,088,904 A * | 2/1992 | Okada | ........... | F04B 43/082 417/474 |
| 5,280,675 A * | 1/1994 | Orsini, Jr. | ........... | B21D 53/845 29/888.1 |
| 5,549,460 A * | 8/1996 | O'Leary | ........... | F04B 43/082 417/474 |
| 6,185,969 B1 * | 2/2001 | Jaubert | ........... | B21D 7/021 72/175 |
| 7,955,060 B2 * | 6/2011 | Gottschalk | ........... | F04B 43/082 417/477.1 |
| 10,480,356 B2 * | 11/2019 | Sung | ........... | F16D 1/06 |
| 2016/0158437 A1 * | 6/2016 | Biasi | ........... | F04B 53/08 604/500 |

FOREIGN PATENT DOCUMENTS

WO WO-2017176015 A1 * 10/2017 ............ F16D 1/06

* cited by examiner

*Primary Examiner* — Charles G Freay
*Assistant Examiner* — Lilya Pekarskaya
(74) *Attorney, Agent, or Firm* — Volpe Koenig

(57) ABSTRACT

An improved linear peristaltic pump that is able to be manufactured using fewer parts while also improving the performance and the reliability of the pump. The linear peristaltic pump utilizes a leaf spring in direct contact with a tube and is therefore able to provide smooth transitions in the forces exerted on the tube.

18 Claims, 14 Drawing Sheets

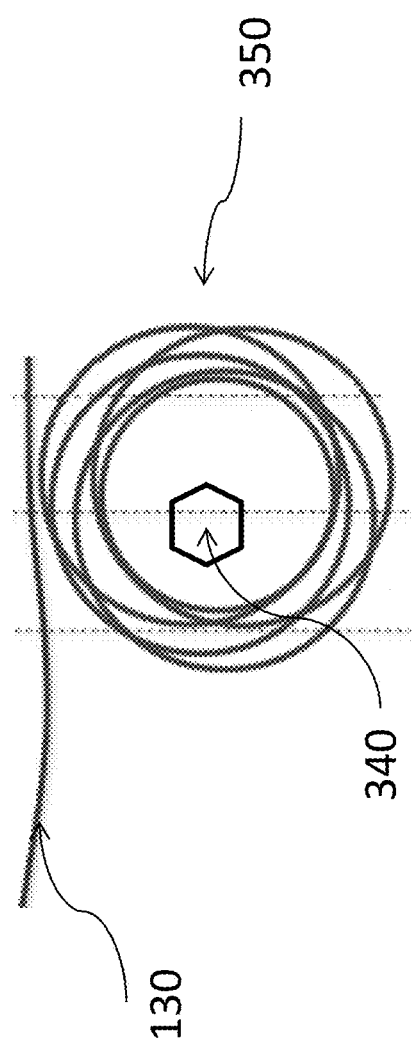

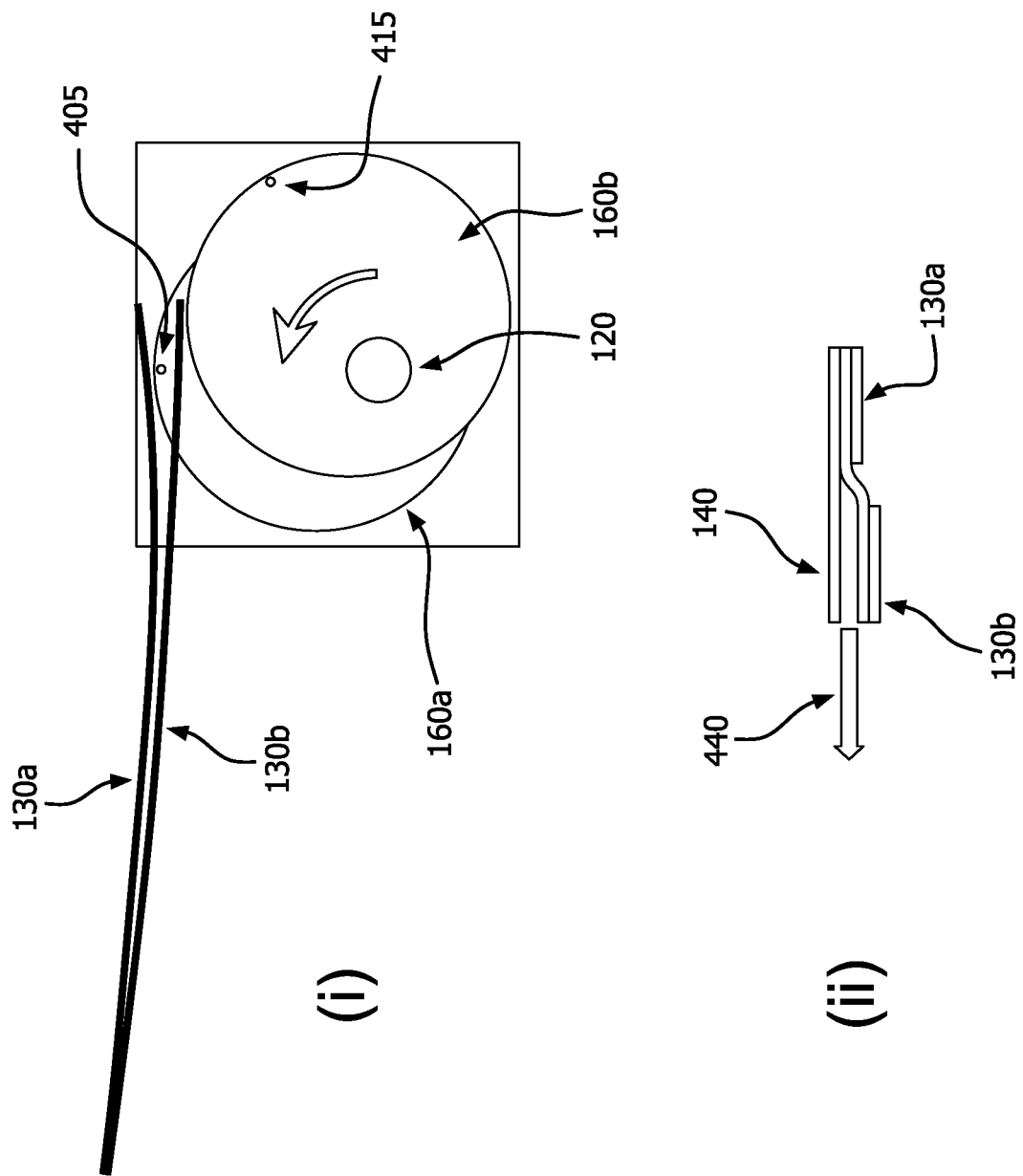

LINEAR PERISTALTIC PUMP

FIELD OF INVENTION

The field of invention relates to positive-displacement pumps and more specifically to linear peristaltic pumps for medical applications.

BACKGROUND

Linear peristaltic pumps are an example of a positive-displacement pump. In a typical linear peristaltic pump, discrete translational elements compress a straight section of flexible tube, moving fluid volumes. By controlling the rate at which the translation elements compress the flexible tube, the flow rate of the fluid can be controlled.

Linear peristaltic pumps are typically used to maintain the sterility of the fluid while the fluid is pumped. Most commonly, peristaltic pumps are used for medical applications including pumping IV fluids through an infusion device. In medical applications, the linear peristaltic pump may be implemented in the patient, affixed to the patient's skin as a "Patch Pump" or integrated into a larger life sustaining system such as a "heart-lung machine."

Several forms of linear peristaltic pump are known in the art. For example, U.S. Pat. No. 4,909,710 to Kaplan et al., which is hereby incorporated by reference, describes a common linear peristaltic pump. In Kaplan's pump, discrete "fingers" compress a tube as a camshaft is rotated. The discrete "finger" configuration causes there to be abrupt changes in the flow rate of the fluid and the pressure experienced by the tube as a result of one "finger" engaging while the other "finger" is disengaging.

Another form of linear peristaltic pump that is known in the art is typified by U.S. Pat. No. 5,158,437 to Natwick et al., which is hereby incorporated by reference. In Natwick's pump, discrete "plungers" directly compress a tube as the shaft rotates. Each discrete "plunger" requires a biasing spring that prevents the plunger from twisting or moving laterally away from the reciprocation axis. The inclusion of a spring on each "plunger" results in a more complex linear peristaltic pump that is more difficult to assemble and still produces the abrupt changes in pressure and flow rate.

SUMMARY

Described herein is an improved linear peristaltic pump that is able to be manufactured using fewer parts while also improving the performance and the reliability of the pump. The linear peristaltic pump utilizes a leaf spring in direct contact with a tube and is therefore able to provide smooth transitions in the forces exerted on the tube. The leaf spring has a number of "fingers" that corresponds to the number of circular cams utilized in the pump. Each "finger" of the flexure provides the function formerly accomplished by a lifter and an over travel compensating spring. Because all leaves of the flexure are integrated into one, easily manufactural comb, the linear peristaltic pump is improved by reducing the component count, decreasing the size of the linear peristaltic pump, increasing the manufacturability while also increasing the speed, accuracy and efficiency of the linear peristaltic pump.

In addition, by using a leaf spring, the mass of the moving parts is minimized. The reduced mass allows the linear peristaltic pump to run at a high number of revolutions per minute. The leaf spring also limits how far the tube opens each cycle so that it stays in the most efficient flow region. This enables the Flexure linear peristaltic pump to be small, simple, efficient and accurate when compared to other linear peristaltic pumps.

BRIEF DESCRIPTION OF THE DRAWING(S)

FIG. 3D is a graphical depiction of the asymmetric rotation of the circular cam.

FIGS. 4A-4C are a graphical depiction of the plurality of circular cams engaging the fingers of the leaf spring.

DETAILED DESCRIPTION OF THE PREFERRED EMBODIMENTS

Figure 1:
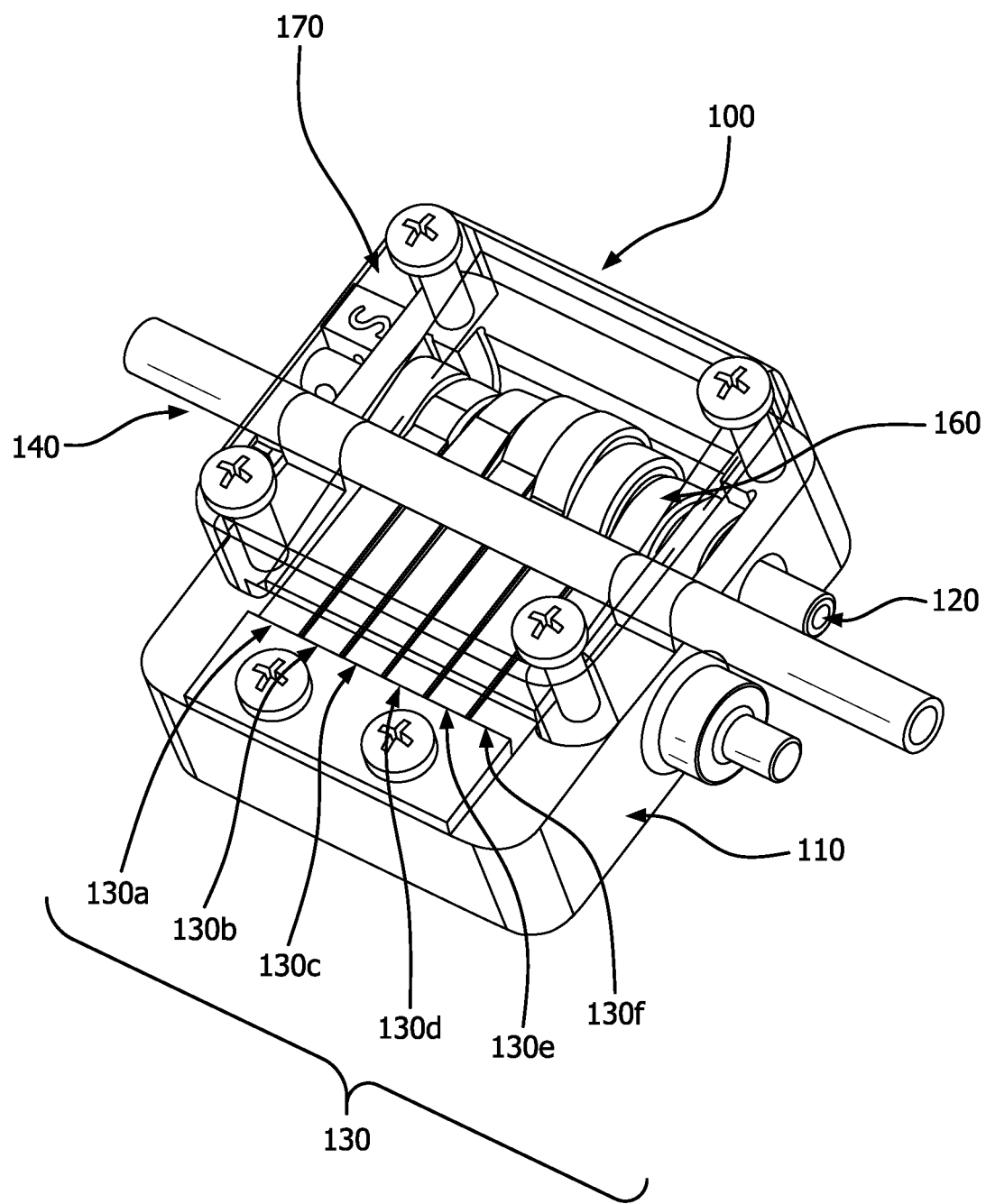
FIG. 1 is a graphic depiction of a linear peristaltic pump in accordance with an embodiment.

FIG. 1 shows an example linear peristaltic pump 100. The linear peristaltic pump 100 includes a housing 110 that supports a camshaft 120. Mounted on the camshaft 120 are a plurality of offset circular cams 160. The rotation of the camshaft 120 causes displacement of the fingers 130a, 130b, 130c, 130d, 130e, and 130f of the leaf spring 130. The number of fingers of the leaf spring 130 corresponds to the number of circular cams 160. Although six fingers are depicted, a person of ordinary skill would appreciate that any number of circular cams 160 and fingers may be used.

The displacement of each finger of the leaf spring 130 causes the respective finger to impinge on the tube 140. The fingers increasingly impinge on the tube 140 as the circular cams 160 rotate from a point of minimum displacement to a point of maximum displacement. Further, the fingers of the leaf spring 130 decreasingly impinge on the tube 140 as the circular cams 160 rotate from a point of maximum displacement to a point of minimal displacement. The resulting deformation of the tube 140 is further described in FIG. 6A discussed below. A cover 170 is in contact with the side of the tube opposite circular cams 160.

Figure 2B:
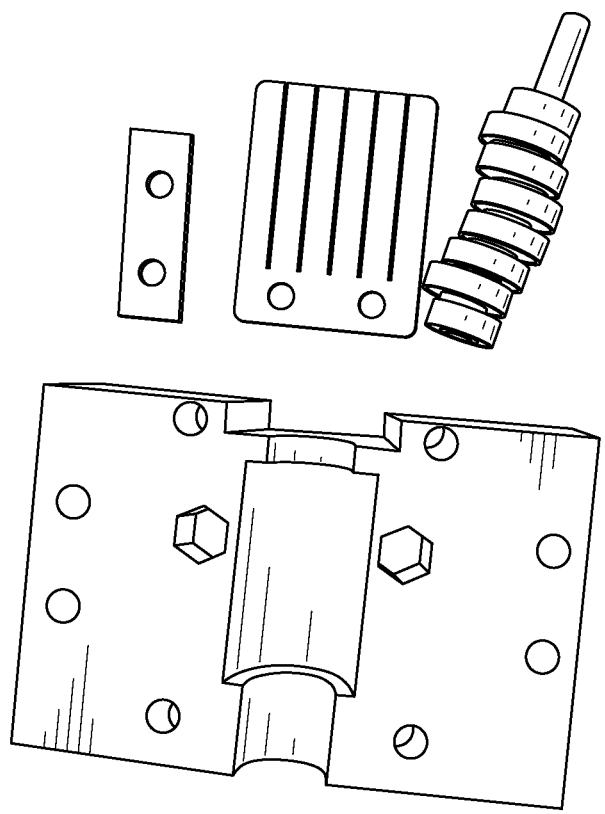
FIG. 2B is a graphic depiction of the number of parts required to form an example linear peristaltic pump according to an embodiment.
Figure 2A:
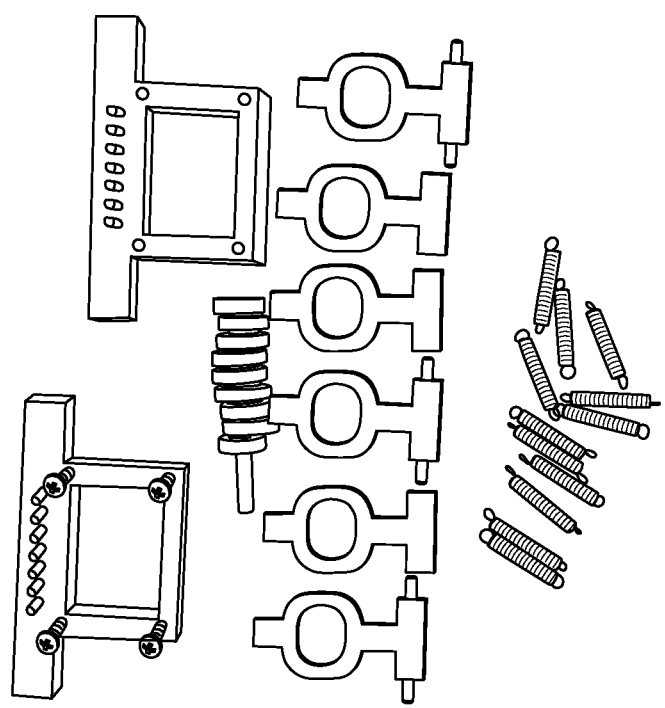
FIG. 2A is a graphic depiction of the number of parts required to form the prior art linear peristaltic pump.

By using the leaf spring 130, the number of parts in linear peristaltic pump 100 is reduced. For example, FIG. 2A depicts the number of parts required in a conventional linear peristaltic pump, such as Natwick's (discussed above). FIG. 2B, on the other hand, depicts an example number of parts required by embodiments of the present invention.

Figure 3C:
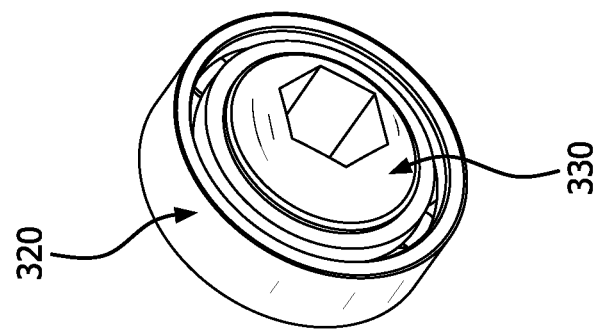
FIG. 3C is a graphical depiction of a cam shaft insert.
Figure 3B:
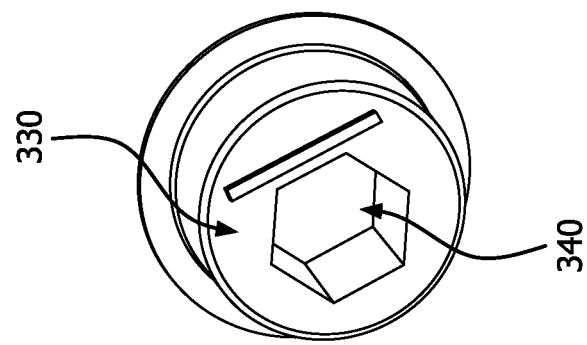
FIG. 3B is a graphical depiction of a cam shaft insert.
Figure 3A:
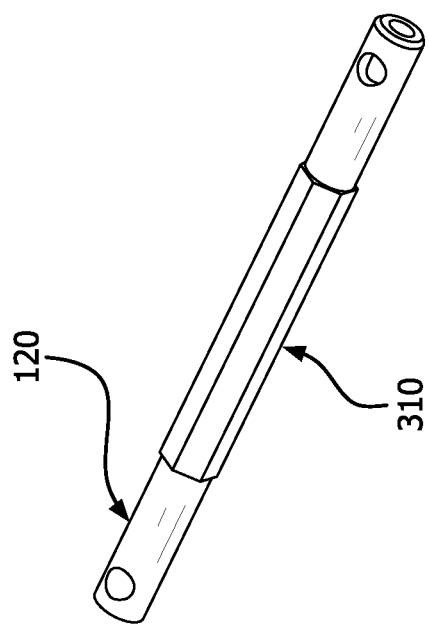
FIG. 3A is a graphical depiction of a cam shaft.

The camshaft 120 may include a hexagonal portion 310 as shown in FIG. 3A. Alternatively, the entire cam shaft 120 may be hexagonal. The hexagonal portion 310 allows for the connection of the cam insert 330 as shown in FIG. 3B. The hexagonal portion 310 of the camshaft 120 is inserted through hole 340. The hole 340 has a complementary shape to the hexagonal portion. The hole 340 is offset from the center of the cam insert 330. The offset through hole 340 causes the circular cam 160 to have an asymmetric rotation 350 about the camshaft 120. The cam insert 330 enables the connection of the ball bearings 320 to hexagonal portion. It is the ball bearings 320 that contact the leaf spring 130. To form the plurality of circular cams 160, the cam insert 330 may be indexed about the hexagonal portion 310. This may enable a further reduction in the number of parts required to produce the linear peristaltic pump 100. As shown in FIG. 3C, the cam insert 330 may be press fit or welded to the ball bearings 320.

The asymmetric rotation 350 of the circular cam 160 is depicted in FIG. 3D. The asymmetric rotation 350 causes the circular cam 160 to have a point of maximum displacement and a point of minimal displacement with respect to leaf spring 130.

Figure 4B:
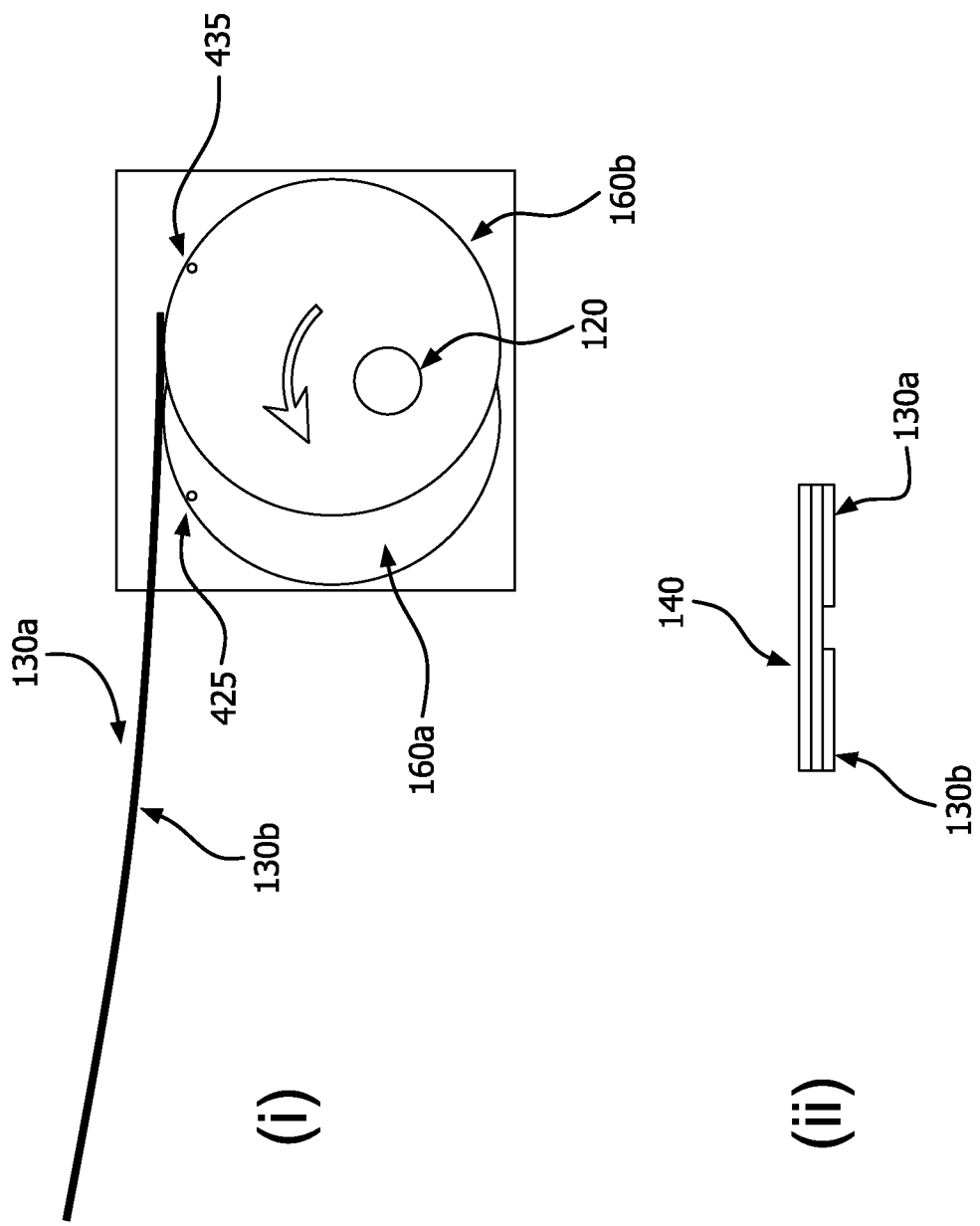
Figure 4C:
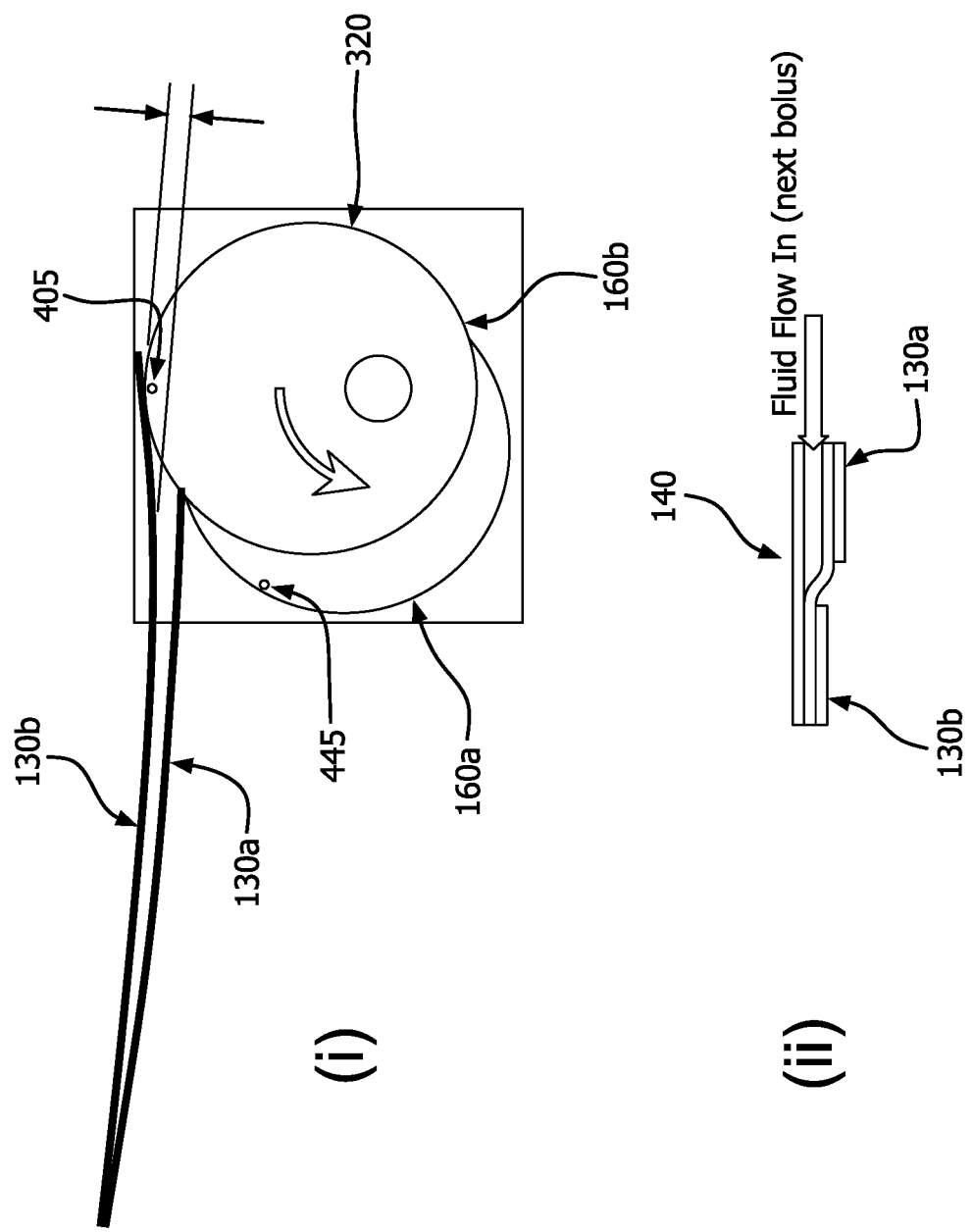

Due to the necessity for a peristaltic pump to be an interference device, a means for lost motion must be incorporated. As a result in embodiments of the linear peristaltic pump 100, the lost motion is provided by over travel of the leaf spring 130, beyond the tube pinch point. Because the lost motion and dwell are both accomplished via spring flexing, the lifter can be a standard, round, low friction ball bearing that is offset from the centerline of the cam shaft 120. FIGS. 4A-4C show the handoff sequence between two adjacent fingers (e.g. 130a and 130b).

In FIG. 4A the circular cam 160b is at point 415 that is 60 degrees before TDC while the circular cam 160a is a TDC point 405. The flow through the tube 140 when the circular cam 160 is at point 405 and 415 is illustrated in section (ii). As the lifters continue to rotate, finger 130a begins to relax while finger 130b continues to flex, forcing fluid above the finger 130b space to flow in direction 440.

In FIG. 4B, the shaft 120 has rotated 30 degrees Counter Clock Wise (CCW) from the position illustrated in FIG. 4A(a). In the position shown in FIG. 4B, circular cams 160a and 160b are at the same height, and the tube 140 is sealed by both fingers 130a and 130b. The near lifter 160b has gone up while the far lifter 160a has come down. As shown in section (ii), in this orientation the tube 140 is completely sealed by fingers 130a and 130b even though neither circular cam 160a or 160b is at TDC 405. Instead, circular cams 160a and 160b are located at +30 degrees (425) and −30 degrees (435), respectively. For example, when finger 130b is 30 degrees before top dead center (BTDC), the tube is closed. Beyond that point, the tube becomes the fulcrum for finger 130b while the circular cam 160b continues toward to top dead center (TDC). At the same time, finger 130a is relaxing from the 30 degrees of over-travel while maintaining the respective tube pinch point closed. In many embodiments, this is where the constant radius section (dwell) would end on the circular cam 160a and would begin on the circular cam 160b.

FIG. 4C shows the system when the leaf 130a has returned the majority of its stored energy back into the system. Specifically, FIG. 4C shows the fingers (e.g. 130a, 130b) of the leaf spring 130 bending about the tube 140 as the circular cams 160 rotate to TDC (405). In FIG. 4C, the circular cam 160a is at position 445 that is +60 degrees past TDC and offset 160b is at TDC 405. This results in the deformation of the tube 140 depicted in section (ii). For example, finger 130a has relaxed to the point where the tube can begin refilling with the next bolus.

Beyond TDC, much of the stored energy in the leaf spring 130 will be returned to the system through the respective low friction ball bearing 320. Because of the very low lifter (flexure) mass, the Flexure Pump can be run at very high RPM without float concerns. This is because reciprocating parts are being accelerated and decelerated up and down through each half rotation. Higher RPM requires higher acceleration. Because the force required to move a lifter is related by mass x acceleration, for a given force, acceleration (RPM) can be increased if the mass of the reciprocating part is decreased. By eliminating the typical intermediate lifter component, the mass of the reciprocating component in the linear peristaltic pump 100 has been reduced to only the leaf spring 130.

Although FIGS. 4A-4C are illustrated with respect to circular cams 160A, 160B and fingers 130a, 130b, a person of ordinary skill in the art would appreciate that the handoff sequence between any two adjacent fingers on the leaf spring 130 will have similar properties to those discussed above.

In many embodiments, the plurality of circular cams 160 are configured so that two circular cams are at their maximum displacement at a same point in the rotation of the camshaft 120. This allows no return flow (leakage) backward through the peristaltic tube. The need for a profiled cam carries the expense of complexity. Because reducing friction against a machined cam requires a bearing and axle, those items must be assembled onto each mechanical lifter. As discussed, adding mass decreases the efficacy of the pump and decreases the maximum number of RPM. Therefore, by adding more mass, a ball bearing and a shaft, increases the mass of the reciprocating part which in turn reduces the maximum RPM. As a result, an increase in lifter mass also leads to flow limitations by limiting high pump RPM.

Figure 5:
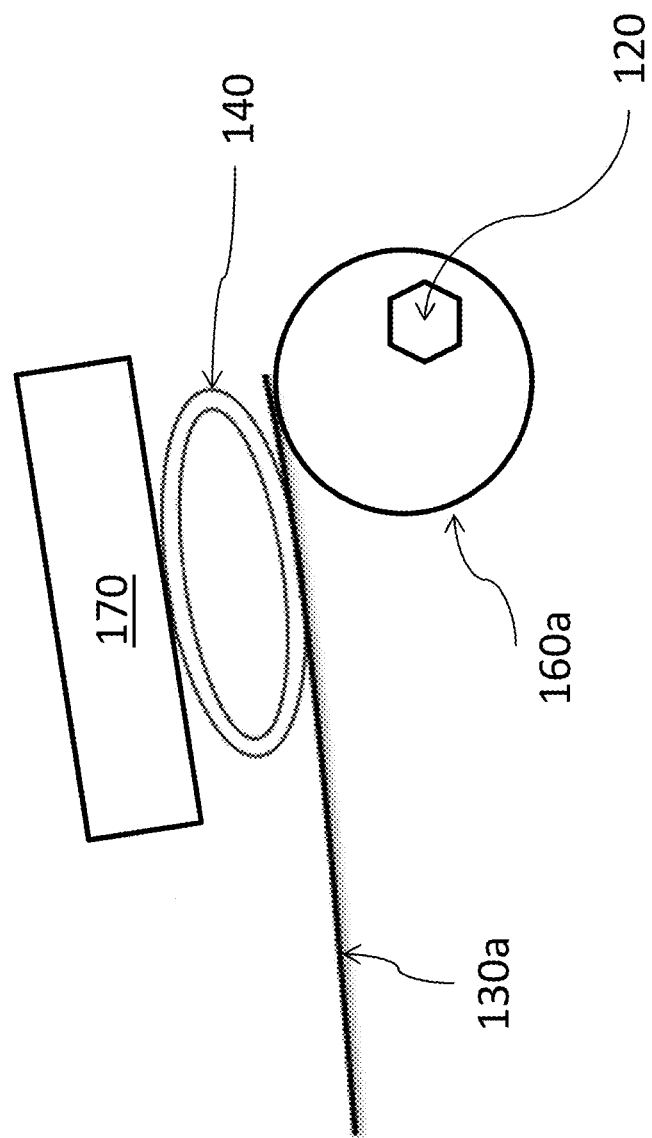
FIG. 5 is a graphical depiction of the deformation of the tube caused by the engagement of the fingers of the leaf spring.

The deformation of the tube 140 caused by the engagement of the fingers of the leaf spring 130 is depicted in FIG. 5. As the camshaft 120 rotates, the circular cam 160a traces an asymmetric path which causes increasing displacement of the finger 130a of the leaf spring 130. The increasing displacement of the finger 130a causes a corresponding deformation in the tube 140. On a 6 actuator pump, when the cam is 30 degrees BTTC, the tube is completely pinched, fluid flow is restricted, and the finger 130a has reached its maximum displacement at that tube location. Between that point and TDC, the flexure continues to bend with the tube as its fulcrum.

Figure 6A:
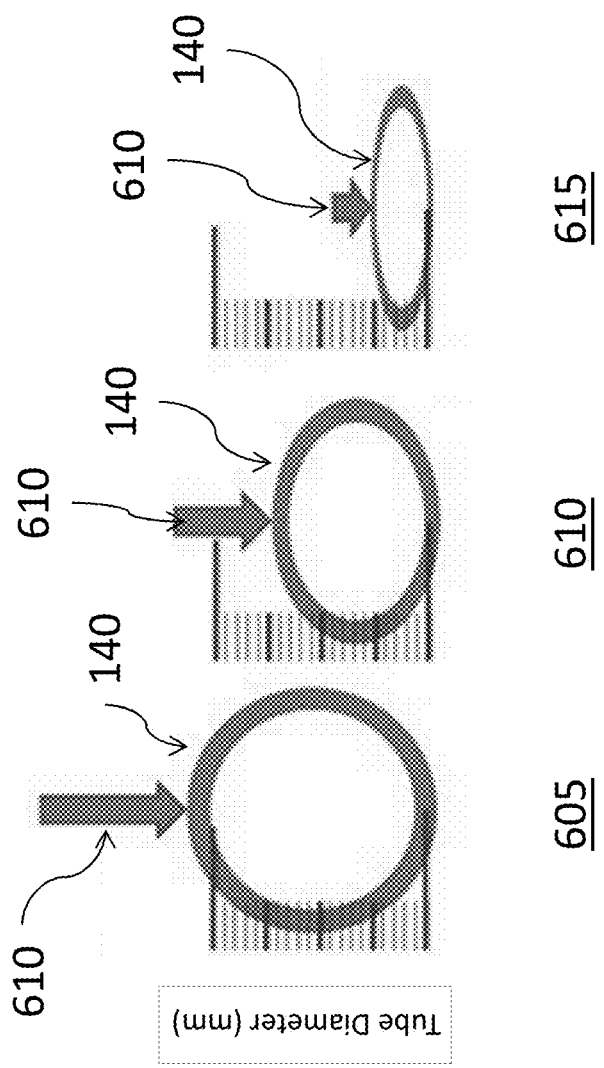
FIG. 6A is a graphical depiction of the deformation of the tube.

FIG. 6A depicts the deformation of the tube 140 as a result of being squeezed. Specifically, 605 shows the maximum diameter when the cross sectional area of the tube is circular. 610 and 615 show the effects of increasing the displacement 610 of an actuator on the diameter in a direction perpendicular to the axis of rotation of the camshaft 120. For example, 615 shows the tube 140 when subjected to a greater displacement than in 610 or 605.

Figure 6B:
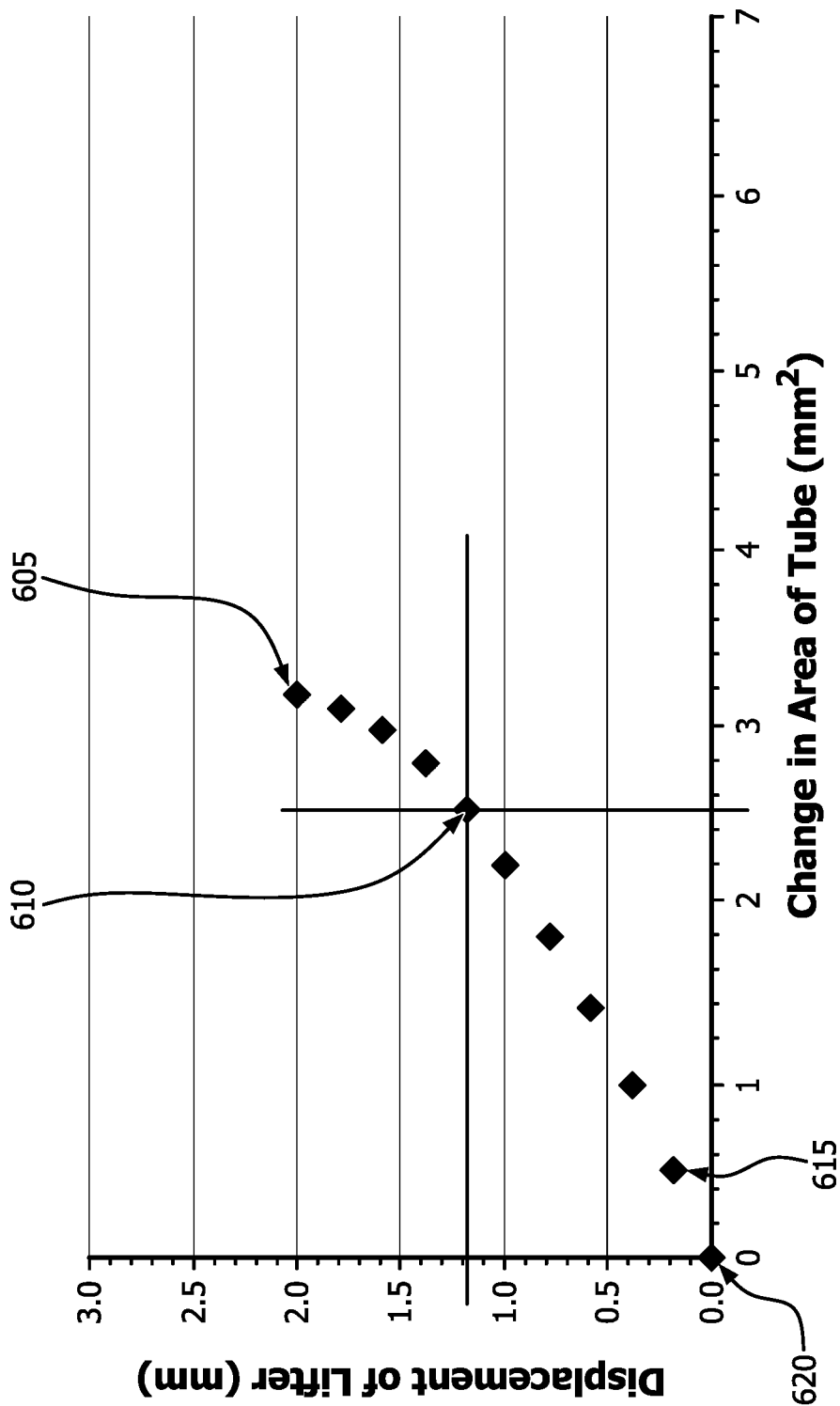
FIG. 6B is a graph of the tube diameter as a function of flow rate.

FIG. 6B graphically correlates the amount of lifter displacement required (vertical axis) to the change in the cross sectional area of a tube 140 (horizontal axis). Specifically, the nearer to being closed the tube is, the greater the change in cross sectional area for a given amount of actuator movement. If the dots were vertical, there would be no flow regardless of how much the tube was displaced. If the dots were horizontal, there would be infinite flow with no tube displacement. Of course, neither of these extremes can be attained, but hydromechanical efficiency is improved when the pump is designed to limit the cross sectional area of the tube by restraining it from opening entirely.

Figure 6C:
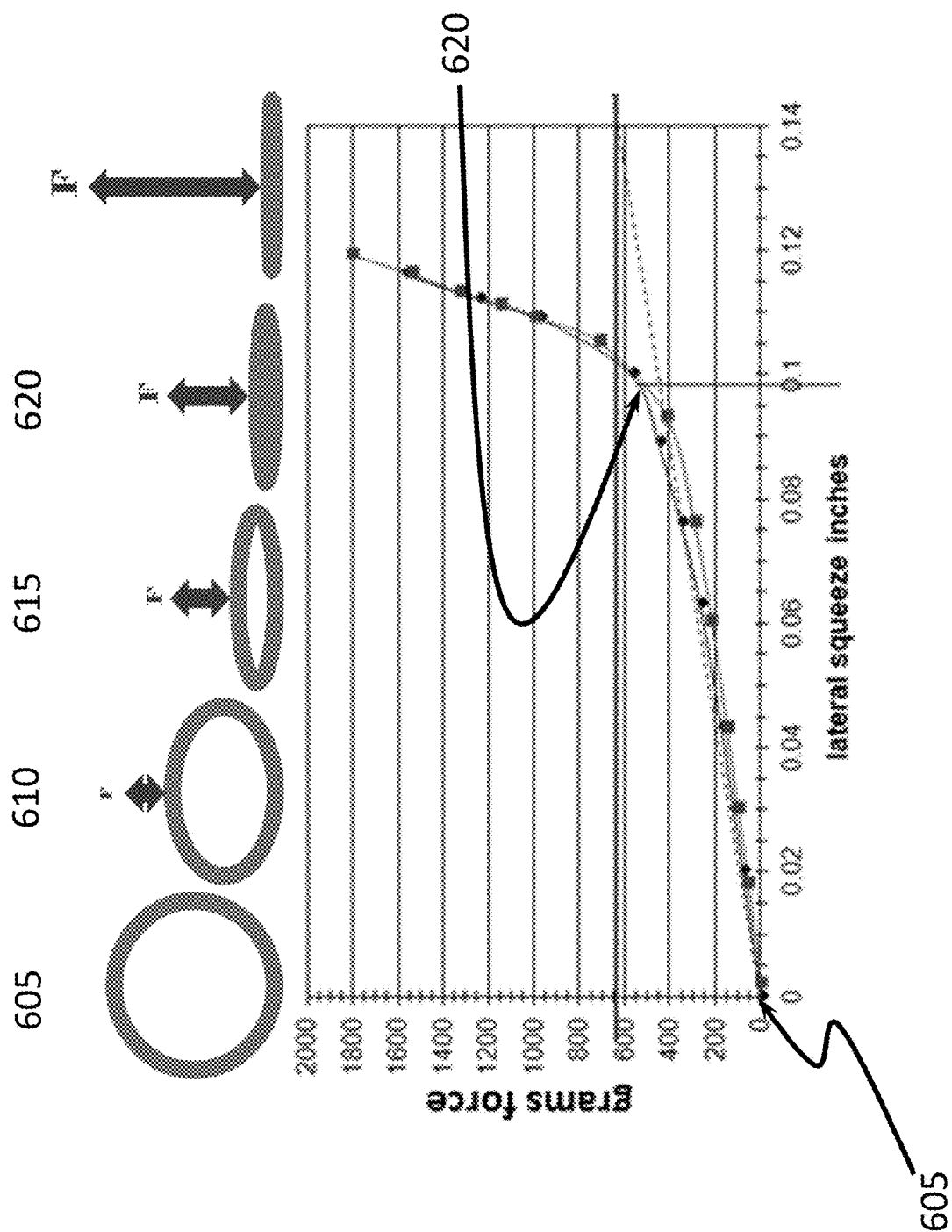
FIG. 6C is a graph of the force required to deform the tube.

A second and equally important reason for not allowing the tube to open entirely is because there is more strength in the tube for drawing in fluid at elevated speeds. FIG. 6C shows the relationship between the force exerted by the tube vs. its diameter. The tube is round at the left side of the chart and gets squeezed toward the right. The inflection point is where the tube is just sealed shut and further displacement expends energy squeezing the wall of the tube. To seal the tube, the force of the leaf spring 130 must operate to the right of the inflection point (at forces above the horizontal line) throughout the dwell portion of the cycle. To fill, there is only the wall strength of the tube to provide the force for overcoming mechanical acceleration of the expanding tube as the actuator retracts and any negative head pressure of the fluid being drawn in. If the wall force is not great enough to accomplish both of these requirements, a gap between the actuator and the tube will occur (float) and pump displacement accuracy will diminish.

For example, from the inflection point back to the left, as the minor diameter of the tube increases, the amount of force that the tube possesses for drawing in more fluid decreases. The less strength the tube has to draw replenishment fluid in, and the slower the pump must turn in order to maintain complete fill and pump accuracy. Therefore, in many embodiments, the leaf spring 130 is configured so that at a point of minimal displacement of the fingers 130a-130f, the gap between the leaf spring and the body 170 is such that the cross sectional area of the tube 140 is restricted from expanding to a circular shape.

The points 615, 610 and 605 correspond to the shapes of the tubes shown in FIG. 6B. At point 620, an inflection point occurs. After point 610, an increase in tube diameter results in smaller increases in the flow rate. Accordingly, in some embodiments, the leaf spring 130 and the circular cams 160 are configured so that at the minimum displacement of the fingers of the leaf spring 130, the cross sectional area of the tube is less than the maximum possible diameter of the tube 140.

Figure 7:
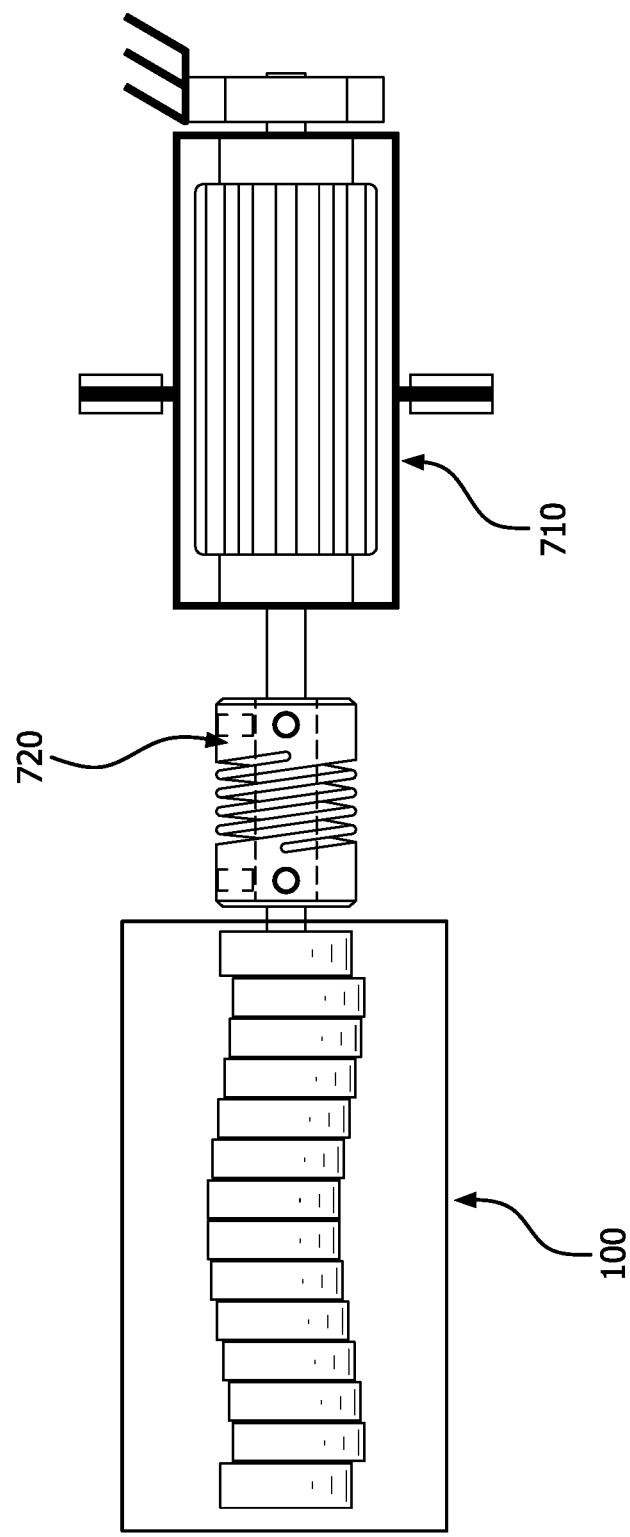
FIG. 7 is a graphical depiction of motor mated to the linear peristaltic pump.

FIG. 7 depicts an embodiment where the linear peristaltic pump 100 is connecting to a motor 710. The motor 710 causes the camshaft 120 to rotate. The motor 710 may be controlled to cause the linear peristaltic pump 100 to dispense a specific amount of fluid or obtain a specific flow rate. The motor 710 may be of any form known in the art, such as a brushed, servo or stepper motor. Due to the fact that a peristaltic pump generates a pulsating bolus flow, overall flow precision can only be attained on a per revolution basis. Having a known "home" position per revolution is worth more than a high resolution encoder for attaining accuracy. Though qualification tests like the International Electrotechnical Commission (IEC) 60601 are fixed time based tests, dispensing on an integer revolution basis while allowing time to float will provide greater accuracy. Knowing the dispensed volume per revolution allows for the determination. However, in this configuration, tube to tube variations are the largest contributor for dispensing inaccuracies. A highly accurate pump system will self calibrate at each tube change.

In some embodiments, the motor 710 may be connected by a gear box 720 to the camshaft 120. In some embodiments, the gear box 720 allows the camshaft 120 to rotate at a slower rate than the rate of rotation of the motor 710.

Figure 8:
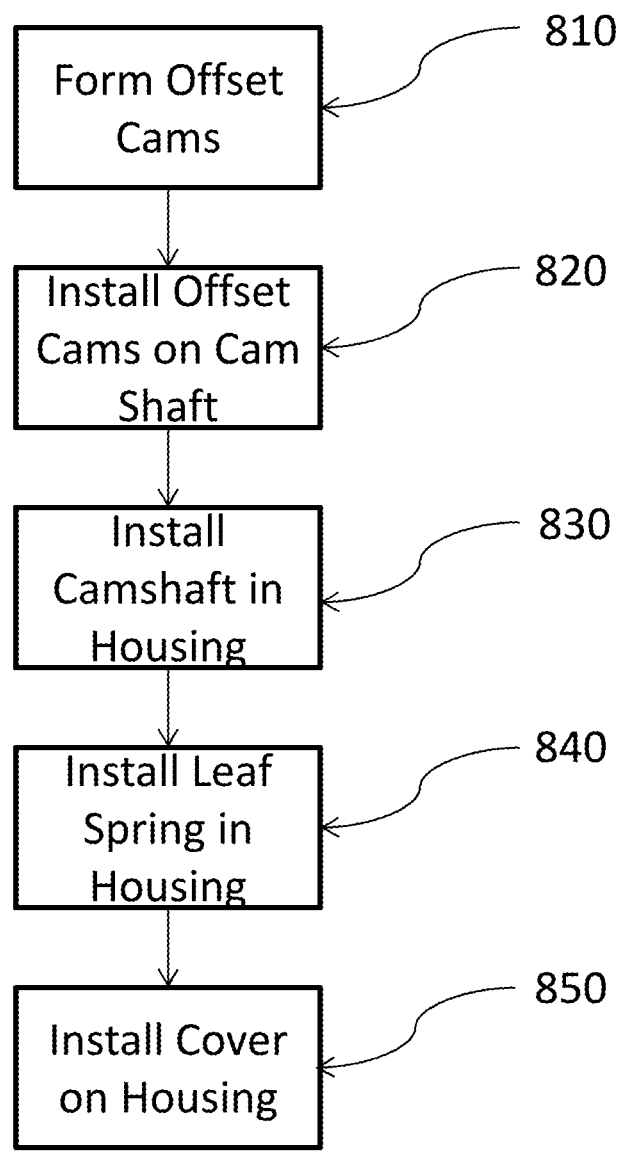
FIG. 8 is a process map for a method of manufacturing a linear peristaltic pump 100.

A process for making the linear peristaltic pump 100 is depicted in FIG. 8. In step 810, the plurality of circular cams 160 are formed by inserting the cam insert 330 into the ball bearings 320. Then, in step 820, the plurality of cams 160 are installed on the camshaft 120. The circular cams 160 are installed on the camshaft 160 to form a sinusoidal pattern by offsetting adjacent camshafts. In addition, the plurality of cam shafts are installed as the camshaft 120 rotates two of the plurality of circular cams 160 at their maximum displacement. Then, in step 830, the camshaft 120 with the plurality of circular cams 160 is installed in the housing 110. In step 840, the leaf spring 130 is installed. The leaf spring 130 is installed with the fingers of leaf spring with each of the plurality of circular cams 160 on the camshaft 120. Finally, in step 850, the cover 170 is installed on the housing 110.

Figure 9:
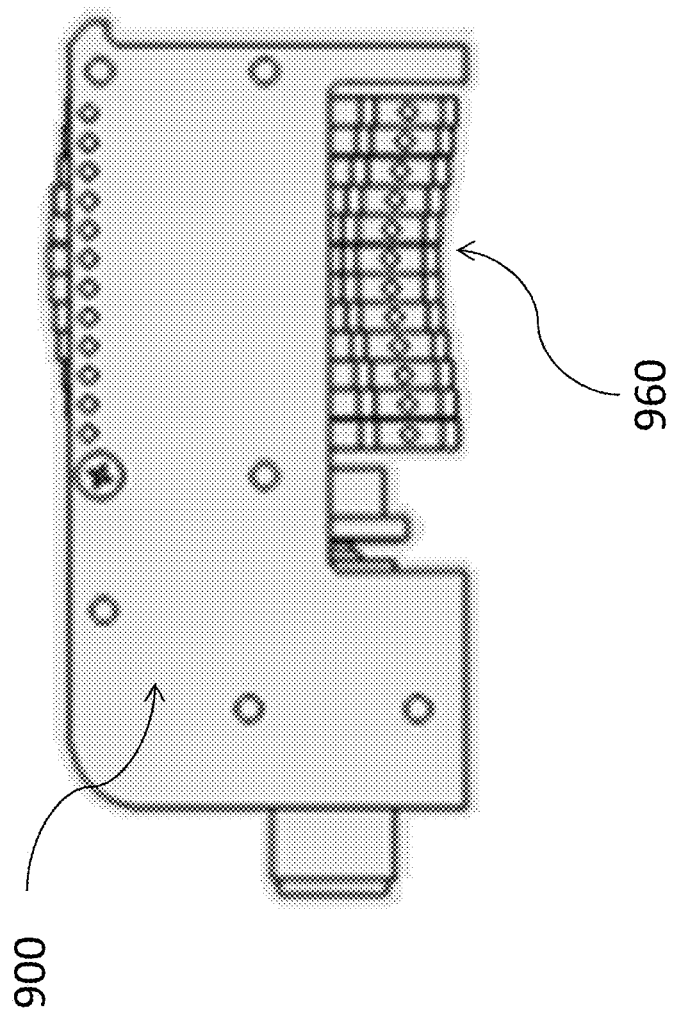
FIG. 9 is a graphic depiction of a linear peristaltic pump with 12 circular cams.

Although embodiments have been discussed with regard to a linear peristaltic pump with six circular cams 160, other numbers of circular cams be utilized provided an even number of circular cams is used. For example, FIG. 9 depicts a linear peristaltic pump 900 with twelve circular cams 960. For this embodiment, a camshaft with dodecagon portion may be used. Alternatively, cam inserts 330 may be modified to accommodate the additional circular cams.

Theoretically, the more cams there are, the less over travel between lifters is required which in turn raises overall energy efficiency. In addition, the longer the section of tubing that is acting as the peristaltic pump, the greater the volume of fluid that is being transferred in each pump revolution. Both can be advantages but at the expense of footprint and part count. A hex shaft is common and so serves as a cost effective drive shaft alternative. In the eccentric insert shown in FIG. 3B, there is a hex hole with the flats oriented in the direction of the maximum offset. This is adequate for a six lobed cam shaft where indexing the insert one position on the shaft will rotate the adjacent cam by 60 degrees. By molding the hex so that the flat is 15 degrees off of the axis, the insert can be flipped from one cam to the next, providing a twelve lobed cam on a hex shaft. Manufacturing the hex into the metal inner race of the bearing is a preferred alternative to assembling a separate injection molded eccentric component.

Although features and elements are described above in particular combinations, one of ordinary skill in the art will appreciate that each feature or element can be used alone or in any combination with the other features and elements.

What is claimed is:

1. A linear peristaltic pump comprising:
   a housing that includes a cover;
   a camshaft mounted on the housing;
   a plurality of offset cams mounted on the camshaft; and
   a leaf spring comprising a plurality of unitary fingers having proximal ends integrated into a single comb of unitary construction, each unitary finger of the plurality of fingers having a bendable intermediate portion and a distal end portion affixed to a corresponding, respective offset cam of the plurality of offset cams;
   wherein a flexible tube is inserted between the leaf spring and the cover;
   wherein a rotation of the camshaft causes each respective cam of the plurality of offset cams to displace a respective corresponding distal end of each unitary finger of the plurality of unitary fingers of the leaf spring by a distance corresponding to an offset of the respective, corresponding offset cam from a top dead center of the camshaft, thereby causing a corresponding bending displacement of each of the bendable intermediate portions of the plurality of unitary fingers as the camshaft rotates, such that each respective bendable intermediate portion of each respective unitary finger of the plurality of unitary fingers impinges directly upon the flexible tube and deforms a cross-sectional area of the flexible tube in accordance with the corresponding bending displacement and in a deforming direction.

2. The linear peristaltic pump of claim 1, wherein each respective unitary finger of the plurality of unitary fingers completely restricts flow through the flexible tube at a point of maximum displacement of the respective unitary finger.

3. The linear peristaltic pump of claim 1, wherein each of the plurality of offset cams includes a cam insert that is inserted into a ball bearing, and wherein the distal end portion of each respective, corresponding unitary finger is affixed to the corresponding, respective offset cam via the cam insert.

4. The linear peristaltic pump of claim 3, wherein the camshaft includes a hexagonal portion; and the cam insert includes a hexagonal through hole; and
wherein the plurality of offset cams are connected to the hexagonal portion of the camshaft via the hexagonal through hole of each respective cam insert.

5. The linear peristaltic pump of claim 1, wherein the plurality of offset cams are paired, and each respective cam of a pair causes a maximum displacement of the respective unitary finger in contact with the respective cam at a same point of the rotation of the camshaft.

6. The linear peristaltic pump of claim 1, wherein the plurality of offset cams includes six cams and the plurality of unitary fingers of the leaf spring includes six unitary fingers.

7. The linear peristaltic pump of claim 1, wherein the plurality of offset cams includes twelve cams and the plurality of unitary fingers of the leaf spring includes twelve unitary fingers.

8. The linear peristaltic pump of claim 1, wherein the camshaft is rotated by an electric motor.

9. The linear peristaltic pump of claim 1, wherein the plurality of offset cams are calibrated to dispense a predetermined amount of fluid from the flexible tube for each revolution of the camshaft.

10. A method of manufacturing a linear peristaltic pump, the method comprising: forming a plurality of offset cams; installing the plurality of offset cams on a camshaft, inserting the camshaft in a housing, wherein the camshaft freely rotates within the housing; attaching a leaf spring to the housing, wherein the leaf spring includes a plurality of unitary fingers having proximal ends that are integrated into a single comb of unitary construction, wherein each of the plurality of the unitary fingers having a distal end and a bendable intermediate portion, affixing the distal end of each unitary finger of the plurality of unitary fingers to a corresponding, respective offset cam of the plurality of offset cams via the cam insert; and connecting a cover to the housing; wherein a rotation of the camshaft causes the plurality of offset cams to displace the distal end portions of the plurality of unitary fingers of the leaf spring in accordance with a displacement of the respective, corresponding offset cam from a top dead center of the camshaft, and bending each of the corresponding, respective bendable intermediate portions in accordance with the displacement; the bending of the bendable intermediate portions of the plurality of unitary fingers causing a deformation in a corresponding, respective cross-sectional area of a circular flexible tube inserted between the leaf spring and the cover of the housing.

11. The method of claim 10, wherein each respective unitary finger of the plurality of unitary fingers completely restricts flow through the flexible tube at a point of maximum displacement of the respective unitary finger.

12. The method of claim 10, wherein forming the plurality of offset cams includes inserting the cam insert into a ball bearing.

13. The method of claim 10, wherein installing the plurality of offset cams on the camshaft includes connecting a hexagonal portion of the camshaft via a hexagonal opening of each respective cam insert, whereby each corresponding unitary finger follows a corresponding flat in the hexagonal opening during the rotation of the camshaft.

14. The method of claim 10, wherein the plurality of offset cams are paired, and each respective cam of a pair causes a maximum displacement of the respective unitary finger in contact with the respective cam at a same point of the rotation of the camshaft.

15. The method of claim 10, wherein the plurality of offset cams includes six cams and the plurality of unitary fingers of the leaf spring includes six unitary fingers.

16. The method of claim 10, wherein the plurality of offset cams includes twelve cams and the plurality of unitary fingers of the leaf spring includes twelve unitary fingers.

17. The method of claim 10, further comprising attaching an electric motor that rotates the camshaft.

18. The method of claim 10, wherein the plurality of offset cams are calibrated to dispense a predetermined amount of fluid from the flexible tube for each revolution of the camshaft.

* * * * *